US010687985B2

(12) United States Patent
Lee et al.

(10) Patent No.: US 10,687,985 B2
(45) Date of Patent: Jun. 23, 2020

(54) WOUND DRESSING

(75) Inventors: Bryony Jayne Lee, Deeside (GB);
Stephen Michael Cotton, Nottingham (GB)

(73) Assignee: CONVATEC TECHNOLOGIES, INC., Las Vegas, NV (US)

(*) Notice: Subject to any disclaimer, the term of this patent is extended or adjusted under 35 U.S.C. 154(b) by 316 days.

(21) Appl. No.: 12/437,647

(22) Filed: May 8, 2009

(65) Prior Publication Data

US 2009/0287130 A1 Nov. 19, 2009

(30) Foreign Application Priority Data

May 8, 2008 (GB) .................................. 0808376.8

(51) Int. Cl.
*A61F 13/00* (2006.01)
*A61F 13/36* (2006.01)

(52) U.S. Cl.
CPC .. *A61F 13/00063* (2013.01); *A61F 13/00021* (2013.01); *A61F 13/00995* (2013.01); *A61F 13/36* (2013.01); *A61F 2013/0054* (2013.01); *A61F 2013/00225* (2013.01); *A61F 2013/00229* (2013.01); *A61F 2013/00238* (2013.01); *A61F 2013/00523* (2013.01); *A61F 2013/00548* (2013.01); *A61F 2013/00714* (2013.01);
(Continued)

(58) Field of Classification Search
CPC .......... A61L 15/00; A61L 15/16; A61L 15/44; A61F 13/00; A61F 13/00012; A61F 13/00029; A61F 13/00063; A61F 13/00021; A61F 13/00995; A61F 13/36; A61F 2013/00225; A61F 2013/00229; A61F 2013/00238; A61F 2013/00523; A61F 2013/0054; A61F 2013/00548; A61F 2013/00748; A61F 2013/00753; A61F 2013/00936; B32B 23/00; B32B 23/02; B32B 23/04
USPC ........ 602/44, 45, 56, 76; 424/443, 445, 446, 424/447; 428/292.4
See application file for complete search history.

(56) References Cited

U.S. PATENT DOCUMENTS 3,521,632 A * 7/1970 Graham ................. A41D 13/12
602/41
4,093,765 A * 6/1978 Schmidt ............ A61F 13/15203
162/112
(Continued)

FOREIGN PATENT DOCUMENTS

DE 19746913 10/1997
DE 20118880 1/2002
(Continued)

OTHER PUBLICATIONS

Definition of "join"; www.merriam-webster.com; accessed Feb. 8, 2014.*
(Continued)

*Primary Examiner* — Anna K Kinsaul
*Assistant Examiner* — Caitlin A Carreiro
(74) *Attorney, Agent, or Firm* — Taft Stettinius & Hollister LLP; Ryan O. White

(57) ABSTRACT

A wound dressing is in the form of a strip or a ribbon. The strip or ribbon is made of gel-forming fibers and has longitudinal lines of stitches formed from a thread and transverse lines of stitches formed from a thread.

23 Claims, 1 Drawing Sheet

(52) U.S. Cl.
CPC ............... *A61F 2013/00748* (2013.01); *A61F 2013/00753* (2013.01); *A61F 2013/00936* (2013.01)

(56) References Cited

U.S. PATENT DOCUMENTS

| | | | | |
|---|---|---|---|---|
| 5,807,295 | A * | 9/1998 | Hutcheon | A61F 5/01 602/42 |
| 2007/0042024 | A1 * | 2/2007 | Gladman | A61F 13/0273 424/445 |
| 2007/0212520 | A1 * | 9/2007 | Furumori et al. | 428/134 |

FOREIGN PATENT DOCUMENTS

| | | | |
|---|---|---|---|
| DE | 20118880 U1 | 1/2002 | |
| GB | 1322936 | 7/1973 | |
| JP | 3431628 B2 * | 7/2003 | |
| WO | WO9311805 | 6/1993 | |
| WO | WO-9311805 A1 | 6/1993 | |
| WO | WO9312275 | 6/1993 | |
| WO | WO9416746 | 8/1994 | |
| WO | WO9846818 | 10/1998 | |
| WO | WO 9967456 A1 * | 12/1999 | ............ A61L 15/28 |
| WO | WO0001425 | 1/2000 | |
| WO | WO0243743 | 6/2002 | |
| WO | WO2007003905 | 1/2007 | |

OTHER PUBLICATIONS

International Application No. PCT/GB2009/001138 International Search Report and Written Opinion dated Aug. 21, 2009.
Trumble et al.: My Sewing Dictionary; http://sewinganswers.com/DNLDG1/Dictionary/MySewingDictionary507.pdf accessed Aug. 13, 2019.

* cited by examiner

WOUND DRESSING

This invention relates to a wound dressing, in particular, to ribbon or strip dressing of the type composed of gel-forming fibers in the form of a woven or nonwoven layer or layers. In particular, the invention relates to dressings comprising gel-forming fibers used in the treatment of sinus or cavity wounds or post-operative wounds.

BACKGROUND OF THE INVENTION

It is known to use carboxymethylated cellulosic materials in situations where a high degree of exudate absorption is required. For example, WO 93/12275 describes the production of various absorbent products capable of absorbing many times their own weight of water. This causes the carboxymethylated fibers to form a gel. WO 94/16746 and WO 00/01425 describe the use of carboxymethylated Lyocell materials in wound dressings where the advantages of gel formation in preventing adherence and, therefore, reducing wound damage and pain on removal are discussed.

Known wound dressings comprising gel-forming fibers are essentially flat, rectangular and fairly small, typically 20 cm×15 cm. The usefulness of such dressings is limited with respect to sinus or cavity wounds due to difficulty in removing the dressing from such a wound. The gel-forming fibers gel on absorption of exudate and consequently lose tensile strength once in a gelled state. This presents a problem when the dressing needs to be removed as removal generally is done by pulling the ribbon out of the wound from one end of the ribbon. The loss of tensile strength means that the dressing fragments on removal and has to be removed in many pieces or by flushing.

However, it would be desirable to bring the advantages of gel-forming fiber dressings to cavity wounds by having the dressings available in a strip form with sufficient tensile strength to enable the dressing to be removed in one piece from the wound once it has gelled and to be removed in one piece regardless of which part of the dressing is grasped in the removal.

It is known to form ribbon dressings with a reinforcing scrim in order to improve the tensile strength of the dressing. There are, however, disadvantages in doing so. The scrim detracts from the absorbency of the dressing and can create a physical barrier to absorption. The scrim also renders the dressing opaque which means that the wound and surrounding skin cannot be observed once the dressing is in situ.

It is known to increase the tensile strength of bandages by stitching the bandage along its length with one or more lines of stitching. However, when longitudinal stitching is applied to a thin strip it gives strength only in the stitching direction and restricts how the dressing can be removed.

SUMMARY OF THE INVENTION

The present invention seeks to provide improved wound dressings which mitigate the problems associated with ribbon dressings in cavity or sinus wounds.

We have now found that it is possible to improve the tensile strength of strip dressings in a dry or wet (gelled) state.

Accordingly, the invention provides a wound dressing comprising a layer in the form of a strip and comprising gel-forming fibers, the strip having longitudinal lines of stitches formed from a thread and transverse lines of stitches formed from a thread.

The longitudinal stitching is longitudinal in that it is generally parallel to the long dimension of the strip.

The transverse stitching is transverse in that it joins the longitudinal lines of stitches together and in some embodiments is generally perpendicular to the long dimension of the strip.

The thread may be a single filament or multiple filament yarn or a staple fiber yarn. The thread can be cellulosic, lycra, nylon, polyester or polyurethane. The thread can be impregnated with an active agent, for example, with an antimicrobial agent.

Such dressings are suited to treating sinus or cavity wounds, post operative or surgical wounds or any wound that needs to be packed. Additionally, such dressings can be used as part of a composite dressing if desired.

The longitudinal stitching preferably passes through the whole thickness of the strip and can be visible on both sides of the strip. The transverse stitching may also pass through the whole thickness of the strip or may be present on one side only of the strip or both.

By gel-forming fibers is meant hygroscopic fibers which upon the uptake of wound exudate become moist slippery or gelatinous and thus reduce the tendency for the surrounding fibers to adhere to the wound. The gel-forming fibers can be of the type which retain their structural integrity on absorption of exudate or can be of the type which lose their fibrous form and become a structureless gel. The gel-forming fibers are, preferably, spun sodium carboxymethylcellulose fibers, chemically modified cellulosic fibers, pectin fibers, alginate fibers, chitosan fibers, hyaluronic acid fibers, or other polysaccharide fibers or fibers derived from gums. The cellulosic fibers, preferably, have a degree of substitution of at least 0.05 carboxymethyl groups per glucose unit. The gel-forming fibers, preferably, have an absorbency of at least 2 grams 0.9% saline solution per gram of fiber (as measured by the free swell method).

Preferably, the gel-forming fibers have an absorbency of at least 10 g/g as measured in the free well absorbency method, more preferably between 15 g/g and 25 g/g.

The dressing may, for instance, comprise non gel-forming fibers and, in particular, may comprise lycra or other elastic fibre.

The dressing may be in the form of 0.5, 1, 2 or more meter lengths and be approximately 0.5 cm to 10 cm wide, preferably from 0.5 cm to 5 cm wide. The longitudinal lines of stitching may be from 1 mm to 10 mm apart and, preferably, from 2 mm to 5 mm apart. The lines of longitudinal stitching may be a lock stitch and may typically be crochet or chain stitch, but other stitch patterns may also be used. The rows of transverse stitching may be from 1 mm to 10 mm apart and, preferably, from 2 mm to 5 mm apart. The transverse lines of stitches may be a pattern stitch and may be crocheted or may be a basting stitch between two layers of superposed gel-forming fibers. Preferably, the lines of stitching are made in a thread such as Tencel®. The transverse stitches serve to link adjacent longitudinal lines of stitches together to add strength to the dressing in a transverse direction. The transverse lines of stitches are preferably made in columns between pairs of adjacent longitudinal lines of stitches with stitch free gaps between the columns to allow a roll of stitched gelling fabric to be slit in the gaps. This allows strips to be formed without creating loose ends of transverse stitching at the edges of the strip.

Preferably, the transverse stitching is made in a continuous zig-zag between longitudinal lines of stitching. The transverse lines of stitching can be perpendicular to the longitudinal stitching as in the case of a zig-zag castellated pattern or at an angle to it as in a continuous zig-zag angled pattern.

Preferably, the dressing comprises at least two longitudinal lines of stitching joined by a transverse line of stitching that runs in a column between the longitudinal lines. This allows the dressing to be slit from a roll with minimal loose ends of thread. More preferably, the dressing comprises at least four longitudinal lines of stitching arranged as two or more pairs of lines where the longitudinal lines of stitching in each pair are joined by a transverse line of stitching in the form of a column. This arrangement allows the user to further cut the dressing in the stitch free gap between the pairs of longitudinal lines of stitching to create a narrower ribbon.

The dressing may comprise one or more medicaments. For example, an antimicrobial agent, or an antibiotic, or an anesthetic on an anti-inflammatory agent, or a skin protective agent, or an odor absorbing agent.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425 to which the reader is directed for further detail.

Desirably, the carboxymethylation is carried out in the presence of industrial methylated spirits (IMS), and IMS is preferably also used in a subsequent washing step, suitably along with water, as a cleaner and sterilizer. The degree of carboxymethylation is desirably such that upon absorption of exudate the fibers at the skin-contacting surface of the bandage form a gel.

In a further aspect, the invention provides a method of manufacturing a wound dressing for use in cavity or sinus wounds characterized in that the method comprises the steps of:

(i) forming a roll of fabric comprising gel-forming fibers;
(ii) stitching the roll with lines of longitudinal stitching;
(iii) stitching the roll with lines of transverse stitching; and
(iv) slitting the roll in a longitudinal direction to form strips.

For example, the roll of fabric can be formed by any convenient method such as making a non-woven web of gel-forming fibers or by knitting a roll of gel-forming fibers. If desired, a non-woven web can be made by hydroentangling a web of Lyocell fibers and carboxymethylating the so-formed web.

Preferably, the transverse stitching is made in columns joining the longitudinal lines of stitching so that stitch free gaps are created between the columns. In this way a ribbon can be slit from the roll in the gaps so that minimal loose ends occur at the edges of the strip which could otherwise be lost into the wound. Preferably, the columns of transverse stitches are secured so that there are no loose threads in the gaps between the columns and the edges of the ribbon or strip have no loose ends. Preferably, the columns of transverse stitches are a continuous line of stitching which zig-zags between the longitudinal lines of stitches. In this way the columns have stitch free gaps in the space between the columns which allow the roll to be slit into strips with no loose ends at their edges. Also, the transverse lines of stitching can be finished at the longitudinal edges of the strip to reduce fraying, and can be made in columns less than the width of the roll.

Preferably, the dressing has several pairs of lines of longitudinal stitching with the lines in each pair joined by transverse stitching in a castellated pattern to create stitch free gaps between adjacent pairs of joined longitudinal lines of stitches. This allows the dressing to be cut into thinner ribbons by the user.

DETAILED DESCRIPTION OF THE PREFERRED EMBODIMENTS

Figure 1:
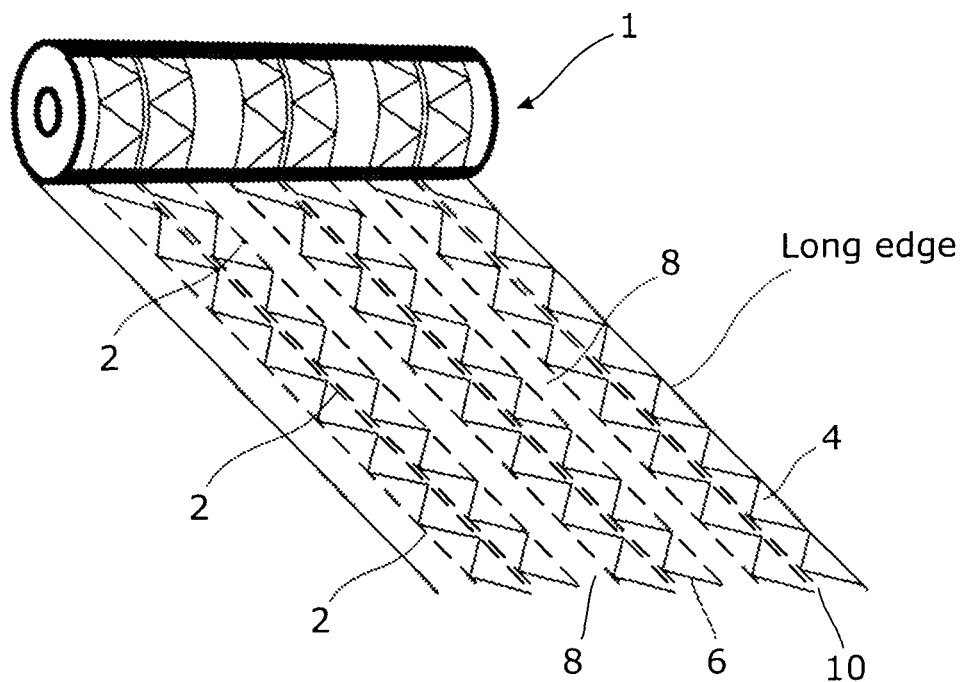
FIG. 1 is a view of a layer of gel-forming fibers in the form of a roll (1) with longitudinal lines of stitching (2) joined by transverse lines of stitching (4) in the form of an angular zig-zag (6) prior to slitting.

FIG. 1 shows a nonwoven roll (1) of gel-forming fibers made by a needle felting carding technique to form a web. Optionally, the roll (1) can have an antimicrobial material incorporated into it and, in particular, silver by the method described in WO 02/43743. The roll is stitched in the longitudinal direction with lines of stitching in Tencel® yarn. The longitudinal lines of stitches (2) are supplemented by transverse lines of stitching (4) in the form of continuous, angular zig-zags (6) which extend between adjacent longitudinal lines of stitches. In this way stitch free gaps (8) are left between columns (10) of longitudinal stitching. The roll is slit in the longitudinal direction in the stitch free gaps (8) to form ribbons.

Figure 2:
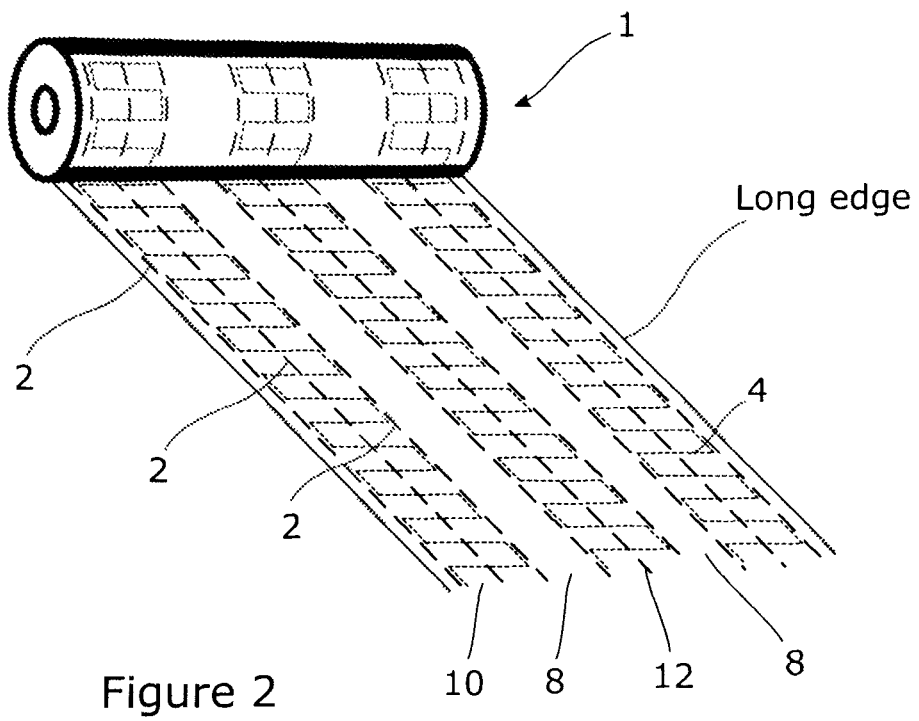
FIG. 2 is a view of a layer of gel-forming fibers in the form of a roll with longitudinal lines of stitching (2) and transverse lines of stitching (4) in the form of a castellated pattern (12) prior to slitting.

FIG. 2 shows a nonwoven roll (1) similar to that shown in FIG. 1 except that the continuous zig-zag of transverse stitches (4) is made in a castellated pattern (12) between the longitudinal lines of stitches (2) and joins them together. The roll is slit in the longitudinal direction in the stitch free gaps (8) to form ribbons.

Preferred embodiments of the invention will now be described with reference to the following examples:

Example 1

Dressing A

A wound dressing was made from a roll of gel-forming fibers as described for the dressing of FIG. 1. The roll had lines of longitudinal stitching spaced 5 mm apart. The column width was 2.5 cm. Ribbons were cut from each roll by slitting in a longitudinal direction at the gaps between the columns in the transverse stitching.

Dressing B

An alternative wound dressing was made by superposing two rolls of gel-forming fibers as described for Dressing A and stitching as described for Dressing A.

Dressing C

An alternative wound dressing was made by eliminating the transverse stitching of Dressing A.

Dressing D

Was formed from 100 gsm Aquacel® a nonwoven dressing made from fibers of carboxymethyl cellulose manufactured by ConvaTec Inc.

Test samples were cut from the stitched rolls to have the dimensions 25 mm wide by 100 mm long for the wet samples and 25 mm wide by 75 mm long for the dry samples. The tensile strength of the gelled and dry samples were measured in the longitudinal and transverse direction in the following manner.

Dry Tensile Testing

Samples were conditioned at 20° C.±2° C. and 65%±4% relative humidity for a minimum period of 24 hours. The samples were secured in the pneumatic jaws of a Zwick® U.T.M. fitted with a 100N load cell. The sample was elongated at a speed of 100 mm/min until a 75% reduction in the sample's maximum force was measured.

Wet Tensile Testing

Samples were conditioned at 20° C.±2° C. and 65%±4% relative humidity for a minimum period of 24 hours. 2 ml of a sodium and calcium chloride solution BP (British Pharmacopeia) was dispensed via a pipette onto the center of the sample and left for a period of 1 minute. The sample was secured within the pneumatic jaws of a Zwick® U.T.M. fitted with a 100N load cell. The sample was elongated at a speed of 100 mm/min until a 75% reduction in the sample's maximum force was measured.

The results are given below where MD=Machine Direction and TD=Transverse Direction.

| Property | Dry Tensile | | Wet Tensile | |
| --- | --- | --- | --- | --- |
| Measurement | MD N/cm | TD N/cm | MD N/cm | TD N/cm |
| Dressing D | 5.33 | 16.19 | 0.16 | 0.42 |
| Dressing B | 8.04 | 20.82 | 4.51 | 4.39 |
| Dressing C | 13.51 | 15.75 | 8.00 | 0.44 |
| Dressing A | 12.19 | 30.78 | 8.05 | 4.45 |

These results show the improvement in tensile strength in transverse stitched samples.

Example 2

Dressing A was used to pack a tracking wound. On removal from the wound the ribbon dressing was fully hydrated with wound fluid yet had maintained its structure. The dressing was easily removed from the wound in one piece.

We claim:

1. A wound dressing comprising a non woven web of gel-forming fibers comprising longitudinal lines of stitches formed from thread and transverse lines of stitches formed from thread extending between at least two longitudinal lines of stitches to form a stitched column between the at least two longitudinal lines of stitches, wherein the transverse lines of stitches are finished at an edge of the at least two longitudinal lines of stitches resulting in at least one stitch free column between stitched columns.

2. The wound dressing of claim 1, wherein said wound dressing is used in cavity wounds or sinus wounds.

3. The wound dressing as claimed in claim 1, wherein the longitudinal lines of stitching are from 1 mm to 10 mm apart and are parallel to a long edge of the wound dressing.

4. The wound dressing as claimed in claim 1, wherein the wound dressing comprises a second non woven web of gel-forming fibers, superposed over the first non woven web of gel-forming fibers wherein the longitudinal lines of stitches join the two non woven web of gel-forming fibers together.

5. The wound dressing as claimed in claim 1, wherein the transverse lines of the pattern stitch are stitched through the wound dressing.

6. The wound dressing as claimed in claim 1, wherein the gel-forming fibers are selected from the group consisting of spun cellulose fibers, chemically modified cellulosic fibers, pectin fibers, alginate fibers, chitosan fibers, hyaluronic acid fibers, other polysaccharide fibers and fibers derived from gums.

7. The wound dressing as claimed in claim 1, wherein the thread is nylon, polyolefin, polyurethane, polyester, cellulosic, or modified cellulosic.

8. The wound dressing as claimed in claim 1, wherein the transverse lines of the pattern stitch are in the form of a continuous zig-zag.

9. The wound dressing as claimed in claim 1, wherein the dressing is used as part of a composite dressing.

10. The wound dressing as claimed in claim 1, wherein the wound dressing is slit in the longitudinal direction in the stitch free gaps so that the dressing has no loose thread from the transverse lines of the pattern stitch at its longitudinal edges.

11. The wound dressing as claimed in claim 1, wherein transverse lines of the pattern stitch are in the form of a castellated pattern.

12. The wound dressing as claimed in claim 1, wherein the wound dressing is slit to form a strip.

13. A method of manufacturing a wound dressing for use in cavity or sinus wounds wherein the method comprises the steps of: (i) forming a roll of fabric comprising a non woven web of gel-forming fibers; (ii) stitching the roll with longitudinal lines of stitching formed from thread; (iii) stitching the roll with transverse lines of stitching formed from thread extending between the longitudinal lines of stitches to form a stitched column and are finished at an edge of at least two longitudinal lines of stitches resulting in stitch free-columns between stitched columns; and (iv) slitting the roll in a longitudinal direction in the stitch free columns.

14. The method as claimed in claim 13, wherein the roll has a width and the lines of transverse stitching are made in columns less than the width of the roll.

15. The method as claimed in claim 14, wherein the dressing has no loose thread from the transverse stitching at its longitudinal edges.

16. The method as claimed in claim 13, wherein the roll of fabric is formed by knitting a roll of gel-forming fibers.

17. The method as claimed in claim 13, wherein the nonwoven web is made by hydroentangling a web of lyocell fibers and carboxymethylating the so formed web.

18. The method as claimed in claim 13, wherein the method comprises the further step of treating the dressing with a source of silver to give antimicrobial properties to the dressing.

19. The method as claimed in claim 13, wherein the method comprises the further step of superposing a second roll of fabric comprising a non woven web of gel-forming fibers on the first a roll of fabric comprising a non woven web of gel-forming fibers before the non woven webs of gel-forming fibers are stitched together.

20. A wound dressing comprising a non woven web of gel-forming fibers, transverse lines of stitches extending between longitudinal lines of stitches to form columns separated by at least one-stitch-free column, wherein transverse lines of stitches are finished at an edge of at least two longitudinal lines of stitches, and wherein the transverse lines of stitches are stitched through the wound dressing.

21. The wound dressing as claimed in claim 20, wherein said wound dressing is used in cavity wounds or sinus wounds.

22. The wound dressing as claimed in claim 20, wherein the gel-forming fibers are selected from the group consisting of spun cellulose fibers, chemically modified cellulosic fibers, pectin fibers, alginate fibers, chitosan fibers, hyaluronic acid fibers, other polysaccharide fibers and fibers derived from gums.

23. The wound dressing as claimed in claim 20, wherein the thread is nylon, polyolefin, polyurethane, polyester, cellulosic, or modified cellulosic.

\* \* \* \* \*